US008989352B2

(12) United States Patent
Laws et al.

(10) Patent No.: US 8,989,352 B2
(45) Date of Patent: Mar. 24, 2015

(54) X-RAY DISTANCE INDICATOR AND RELATED METHODS

(71) Applicant: Aribex, Inc., Orem, UT (US)

(72) Inventors: David J. Laws, Provo, UT (US); Devin Ellsworth, Provo, UT (US)

(73) Assignee: Aribex, Inc., Orem, UT (US)

( * ) Notice: Subject to any disclaimer, the term of this patent is extended or adjusted under 35 U.S.C. 154(b) by 304 days.

(21) Appl. No.: 13/683,804

(22) Filed: Nov. 21, 2012

(65) Prior Publication Data

US 2013/0136238 A1 May 30, 2013

Related U.S. Application Data

(60) Provisional application No. 61/563,737, filed on Nov. 25, 2011, provisional application No. 61/563,793, filed on Nov. 25, 2011.

(51) Int. Cl.
*G21K 1/04* (2006.01)
*A61B 6/08* (2006.01)

(52) U.S. Cl.
CPC ... *A61B 6/08* (2013.01); *G21K 1/04* (2013.01); *G21K 1/046* (2013.01)
USPC ........... 378/147; 378/145; 378/149; 378/150; 378/160

(58) Field of Classification Search
CPC .......... G21K 1/04; G21K 1/043; G21K 1/046
USPC .......................... 378/145, 147, 149, 150, 160
See application file for complete search history.

(56) References Cited

U.S. PATENT DOCUMENTS

| 2,593,873 | A | 4/1952 | Gorey |
| 3,322,950 | A | 5/1967 | Bailey et al. |
| 3,609,370 | A | 9/1971 | Peyser |

(Continued)

FOREIGN PATENT DOCUMENTS

| CA | 2009693 | 3/1991 |
| EP | 0055620 | 7/1982 |

(Continued)

OTHER PUBLICATIONS

International Search Report for PCT/US2012/066355, Feb. 8, 2013, 2 pgs.

(Continued)

*Primary Examiner* — David A Vanore
(74) *Attorney, Agent, or Firm* — Phillips Ryther & Winchester; Matthew D. Thayne

(57) ABSTRACT

Apparatus and methods for providing a distance indication using an x-ray apparatus. According to various embodiments, an x-ray apparatus may be provided comprising an x-ray generator and a visible light generator. The apparatus may further comprise a projection member, such as a reticle, comprising a material at least partially transparent to visible light, wherein the projection member comprises an image positioned within the path of the visible light so as to project a secondary image comprising a shadow defined by the image. A LASER configured to deliver a LASER beam at an angle relative to the visible light may be provided such that the LASER beam intersects at least a portion of the secondary image at a predetermined distance from the LASER to allow a user to determine precisely a distance from the apparatus to an object to be exposed to x-ray radiation.

20 Claims, 9 Drawing Sheets

(56) References Cited

U.S. PATENT DOCUMENTS

| | | | | |
|---|---|---|---|---|
| 3,767,931 A | * | 10/1973 | Williams | 378/153 |
| 3,947,690 A | | 3/1976 | Peyser | |
| 4,100,404 A | | 7/1978 | Johnson et al. | |
| 4,196,351 A | * | 4/1980 | Albert | 378/98.6 |
| 4,229,656 A | * | 10/1980 | Iversen et al. | 378/178 |
| 4,242,587 A | * | 12/1980 | Lescrenier | 378/20 |
| 4,246,488 A | | 1/1981 | Hura | |
| 4,356,400 A | * | 10/1982 | Polizzi et al. | 378/138 |
| 4,380,820 A | | 4/1983 | Cutter | |
| 4,426,726 A | * | 1/1984 | Cheetham | 378/206 |
| 4,465,368 A | | 8/1984 | Matsuura | |
| 5,188,110 A | * | 2/1993 | Sugimoto | 600/425 |
| 5,332,908 A | | 7/1994 | Weidlich | |
| 5,495,336 A | * | 2/1996 | Nose et al. | 356/616 |
| 5,572,568 A | * | 11/1996 | Kanemitsu | 378/206 |
| 5,739,898 A | | 4/1998 | Ozawa et al. | |
| 5,835,555 A | * | 11/1998 | Barry et al. | 378/146 |
| 5,991,362 A | | 11/1999 | Jones | |
| 6,034,764 A | | 3/2000 | Carter | |
| 6,148,062 A | | 11/2000 | Romeas | |
| 6,296,977 B1 | | 10/2001 | Kaise et al. | |
| 6,327,023 B1 | | 12/2001 | Bukofsky et al. | |
| 6,522,717 B1 | * | 2/2003 | Murakami et al. | 378/43 |
| 6,538,740 B1 | | 3/2003 | Shiraishi et al. | |
| 6,583,860 B2 | | 6/2003 | Haga | |
| 6,819,404 B2 | | 11/2004 | Tanaka | |
| 7,224,769 B2 | * | 5/2007 | Turner | 378/98.2 |
| 7,355,682 B2 | * | 4/2008 | Bani-Hashemi | 356/3.1 |
| 7,380,986 B2 | | 6/2008 | Brandstatter et al. | |
| 7,496,178 B2 | * | 2/2009 | Turner | 378/101 |
| 7,516,571 B2 | | 4/2009 | Scrogin et al. | |
| 7,551,715 B2 | * | 6/2009 | Rothschild et al. | 378/57 |
| 7,783,007 B2 | * | 8/2010 | Echner | 378/65 |
| 7,856,750 B2 | | 12/2010 | Sammut et al. | |
| 8,085,903 B2 | * | 12/2011 | Thomas | 378/152 |
| 8,184,776 B2 | * | 5/2012 | Yuan | 378/157 |
| 8,824,638 B2 | * | 9/2014 | Nicholson et al. | 378/150 |
| 2004/0131157 A1 | | 7/2004 | Stevanovic et al. | |
| 2006/0067481 A1 | | 3/2006 | Morton | |
| 2008/0192897 A1 | * | 8/2008 | Piorek et al. | 378/98.8 |
| 2009/0267895 A1 | | 10/2009 | Bunch | |
| 2011/0075805 A1 | | 3/2011 | Machan et al. | |
| 2012/0106714 A1 | * | 5/2012 | Grodzins et al. | 378/146 |
| 2013/0003936 A1 | * | 1/2013 | Grodzins et al. | 378/151 |
| 2013/0044860 A1 | * | 2/2013 | Nicholson et al. | 378/62 |
| 2013/0136238 A1 | * | 5/2013 | Laws et al. | 378/147 |
| 2013/0136239 A1 | * | 5/2013 | Laws et al. | 378/150 |
| 2013/0315368 A1 | * | 11/2013 | Turner | 378/41 |

FOREIGN PATENT DOCUMENTS

| | | |
|---|---|---|
| GB | 424619 | 5/1933 |
| WO | 2009093187 | 7/2009 |

OTHER PUBLICATIONS

Written Opinion for PCT/US2012/066355, Feb. 8, 2013, 7 pgs.
International Search Report for PCT/US2012/066357, Feb. 14, 2013, 3 pgs.
Written Opinion for PCT/US2012/066357, Feb. 14, 2013, 7 pgs.
Unpublished U.S. Appl. No. 13/743,976, filed Jan. 17, 2013.
Unpublished U.S. Appl. No. 13/396,388, filed Feb. 14, 2012.

* cited by examiner

X-RAY DISTANCE INDICATOR AND RELATED METHODS

RELATED APPLICATIONS

This application claims the benefit under 35 U.S.C. §119(e) of U.S. Provisional Patent Application No. 61/563,737 filed Nov. 25, 2011 and titled "X-ray Apparatus with Multiple Adjustments." This application also claims the benefit under 35 U.S.C. §119(e) of U.S. Provisional Patent Application No. 61/563,739 filed Nov. 25, 2011 and titled "Range Finder." Both of the foregoing applications are hereby incorporated by reference in their entireties.

BRIEF DESCRIPTION OF THE DRAWINGS

Non-limiting and non-exhaustive embodiments of the disclosure are described herein, including various embodiments of the disclosure with reference to the figures, in which.

SUMMARY

Figure 1:
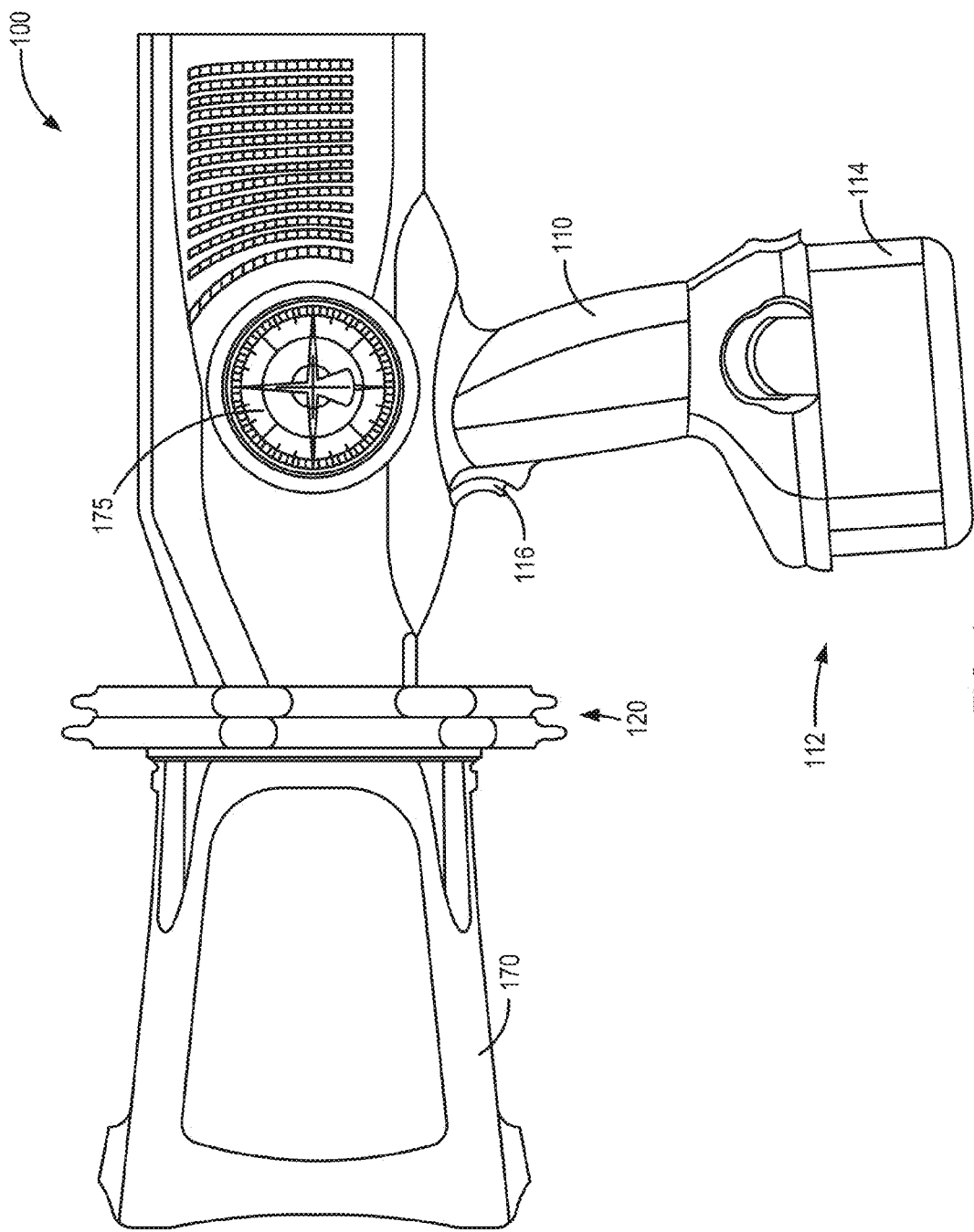
FIG. 1 is a perspective view of one embodiment of an x-ray apparatus.

The present disclosure provides apparatus, systems, and methods relating to the delivery of radiation, such as x-ray radiation, for medical diagnosis and/or treatment.

In x-ray procedures, it may be beneficial for complete and accurate imaging to know where the x-ray beam is being aimed. However, in order to avoid artifacts in the x-ray image, it may be desirable to position an aim light such that it is not arranged in the x-ray beam. Instead, it may be desirable to position an aim light or ranging beam near the x-ray beam. It may also be desirable to not just see a spot or center location of the x-ray beam, but the entire size and shape of the x-ray pattern. Thus, in some embodiments, visible light may be provided that is at least partially coincident and coaxial with an x-ray beam so as to form a light beam of at least substantially the same area as the x-ray beam at any given distance along the respective x-ray and light beams.

The x-ray beam and light beam can both be directed through a collimator, as discussed below, which may shape and size the beams identically and simultaneously. Some embodiments may comprise a collimator comprising a shutter mechanism for collimating x-rays having one or more horizontal shutters and one or more vertical shutters. The movement of the shutters may be accomplished by rotating disks having angled slots that may be coupled with engagement pins or other protruding members on the shutters. The rotation of the disks may be converted to linear motion of the shutters. One disk may be associated with the horizontal shutters and another may be associated with the vertical shutters, thereby allowing for independent movement of each set of shutters. Together, each of the shutters may make up a collimation aperture.

The collimator may be mounted in front of an x-ray generating device to control the shape and/or size of the x-ray beam. The shutters may be aligned to be perpendicular to the centerline of the generated x-ray beam. This allows the center of the x-ray to always be known. In some embodiments, as further discussed below, a visible light source may also be provided that may overlap with the x-ray beam. In this manner a user may be able to fully visualize at least a portion of or, in some embodiments, the full extent of, the x-ray beam being delivered by the device.

In some embodiments, an x-ray apparatus may be provided comprising a first rotatable disk comprising a first plurality of angled slots and a first shutter comprising a first plurality of protruding members. At least one of the first plurality of protruding members may be positioned within a first angled slot of the first plurality of angled slots, and at least one of the first plurality of protruding members may be positioned within a second angled slot of the first plurality of angled slots. This configuration may provide stability to prevent the shutter from pivoting with respect to a single protruding member and/or to prevent binding of the shutters relative to the collimator.

The first shutter may at least partially define an x-ray collimation aperture. The apparatus may also be configured such that rotation of the first rotatable disk results in movement of the first shutter to alter a size of the x-ray collimation aperture.

Some embodiments may further comprise a second rotatable disk comprising a second plurality of angled slots, along with a second shutter comprising a second plurality of protruding members. Similar to the first rotatable disk, at least one of the second plurality of protruding members may be positioned within a first angled slot of the second plurality of angled slots, and at least one of the second plurality of protruding members may be positioned within a second angled slot of the second plurality of angled slots. Again, this configuration may be useful to provide a more stable movement of the shutters along a desired path. The first shutter and the second shutter may at least partially define the x-ray collimation aperture, and the apparatus may be further configured such that rotation of the second rotatable disk results in movement of the second shutter to alter the size of the x-ray collimation aperture.

In some embodiments, the second shutter may be configured to move in a direction at least substantially perpendicular to the first shutter. In other embodiments, the second shutter may be configured to move in a direction at least substantially opposite from the first shutter. In some embodiments, as discussed in greater detail below with reference to the accompanying drawings, four shutters may be provided. In some such embodiments, two shutters may be operably coupled with the first rotatable disk and two shutters may be operably coupled with the second rotatable disk. In some such embodiments, the two shutters operably coupled with the first rotatable disk may be configured to move in directions at least substantially opposite from one another such that these two shutters close towards one another. Similarly, the other two shutters operably coupled with the second rotatable disk may be configured to move in directions at least substantially opposite from one another such that these two shutters close towards one another. However, the two shutters operably coupled with the second rotatable disk may be configured such that they both move in directions at least substantially perpendicular to the directions in which the two shutters operably coupled with the first rotatable disk move.

Some embodiments may further be configured such that the collimation aperture cannot be fully closed. For example, one or more of the shutters may be configured such that movement in a direction to decrease the size of the collimation aperture is prevented before the collimation aperture is entirely closed by the shutters. As described below, this may be useful for certain embodiments that provide a visual indication of an x-ray target such that the visual indication never completely disappears.

In some embodiments, the apparatus may be configured such that the first rotatable disk can be rotated independently of the second rotatable disk. In addition, in some embodiments, the apparatus may be configured such that rotation of the first rotatable disk through a first angle results in movement of the first shutter of a first distance, such that rotation of the second rotatable disk through the first angle results in movement of the second shutter of a second distance, and such that the first distance differs from the second distance. This feature may be useful for embodiments having a rectangular, non-square field-of-view, such as embodiments designed to match up with a 10 inch×12 inch detector, for example. With regard to such embodiments, it may be useful to configure the apparatus such that the horizontal shutters move farther than the vertical shutters for the same amount of rotation of the rotatable disks in order to maintain a constant horizontal to vertical "aspect ratio" throughout at least a portion of the whole range of motion. Some embodiments, however, may be configured such that the smallest size of the collimation aperture is a square.

Some embodiments, however, may be configured such that the aspect ratio changes slightly throughout the rotation. For example, in some embodiments, the largest size of the collimation aperture may be a rectangle with a given aspect ratio, such as 10×12, and the smallest size of the collimation aperture may a square. Thus, the two rotatable disks may be configured such that equal rotation angles result in different shutter movement speed (due to different slot angling between the front and rear rotatable disks) to allow for constant adjustment of the aspect ratio between the two terminal positions.

Alternatively, the apparatus may be configured such that the vertical shutters stop moving before the horizontal shutters stop moving so as to allow the aperture to be changed from its smallest possible rectangular, non-squared shape to a corresponding minimally-sized square.

In some embodiments, the x-ray apparatus may be configured such that the first angled slot extends towards a center of the first rotatable disk at a first angle, such that the second angled slot extends towards the center of the first rotatable disk at a second angle, and such that the first angle is greater than the second angle. In some such embodiments, the first angled slot may have a first radius of curvature, the second angled slot may have a second radius of curvature, and the first radius of curvature may be greater than the second radius of curvature.

In some embodiments, a second shutter comprising a second plurality of protruding members may be provided. At least one of the second plurality of protruding members may be positioned within a third angled slot of the first plurality of angled slots, and at least one of the second plurality of protruding members may be positioned within a fourth angled slot of the first plurality of angled slots. The third angled slot may be configured to extend towards the center of the first rotatable disk at a third angle, wherein the third angle is at least substantially identical to the first angle. The fourth angled slot may extend towards the center of the first rotatable disk at a fourth angle, wherein the fourth angle is at least substantially identical to the second angle.

In some embodiments, one or more of the rotatable disks may further comprise a plurality of protrusions positioned along at least a portion of a perimeter of the rotatable disk(s). Such protrusions may be configured to protrude beyond the perimeter of the rotatable disk(s) adjacent to the protrusions. These protrusions may be configured to allow a user to rotate the rotatable disk(s) in order to alter a size of the collimation aperture.

The protrusions of one rotatable disk may be configured to have at least one of a different shape and a different size relative to the protrusions of another rotatable disk. In this manner, a user may be able to see and/or feel the difference between the two sets of protrusions to provide information about which shutter or shutters will be opened or closed by rotating the disk associated with the protrusions.

In one particular embodiment of an x-ray apparatus, the apparatus may comprise an x-ray generator configured to generate x-ray electromagnetic radiation. The x-ray apparatus may further comprise a visible light generator configured to generate visible electromagnetic radiation. In some embodiments, the visible light generator may comprise a light-emitting diode. The visible light generator may be configured to deliver the visible electromagnetic radiation such that the visible electromagnetic radiation at least partially overlaps the x-ray electromagnetic radiation. In this manner, a user may be able to visualize the path of the x-ray radiation and determine a treatment or diagnosis area defined by the x-ray radiation delivered by the device.

The collimation aperture may be configured to deliver overlapping radiation comprising x-ray electromagnetic radiation from the x-ray generator and visible electromagnetic radiation from the visible light generator, and may be configured to deliver the visible electromagnetic radiation in a visible target shape, and to deliver the x-ray electromagnetic radiation in an x-ray target shape. The size of the visible target shape may vary according to the size of the collimation aperture, and the size of the x-ray target shape may also vary according to the size of the collimation aperture.

The x-ray apparatus may also comprise a first rotatable disk and a first shutter operably coupled with the first rotatable disk such that rotation of the first rotatable disk results in movement of the first shutter to alter the size of the collimation aperture.

The x-ray apparatus may further comprise a mirror that is positioned and configured to reflect light from the visible light generator through the collimation aperture. The mirror may be transparent to x-ray electromagnetic radiation, and may be positioned in between the x-ray generator and the collimation aperture. In such embodiments, the mirror may be further configured such that x-ray electromagnetic radiation from the x-ray generator passes through the mirror before being delivered through the collimation aperture. The mirror may also comprise a silver coating, such as a silver oxide coating. In some embodiments, the x-ray generator may be positioned away from a center of the mirror by a first distance and the visible light generator may be positioned away from the center of the mirror by a second distance. The first distance may be at least substantially identical to the second distance.

In yet another example of an embodiment of an x-ray apparatus, the apparatus may comprise an x-ray generator configured to generate x-ray electromagnetic radiation and a visible light generator configured to generate visible electromagnetic radiation. The visible light generator may be configured to deliver the visible electromagnetic radiation such that the visible electromagnetic radiation at least partially overlaps the x-ray electromagnetic radiation.

The apparatus may further comprise a first rotatable disk comprising a first plurality of angled slots and a second rotatable disk comprising a second plurality of angled slots. The apparatus may also comprise a first shutter comprising a first plurality of protruding members. At least one of the first plurality of protruding members may be positioned within a first angled slot of the first plurality of angled slots, and at least one of the first plurality of protruding members may be positioned within a second angled slot of the first plurality of angled slots. Similarly, the apparatus may comprise a second shutter comprising a second plurality of protruding members, wherein at least one of the second plurality of protruding members is positioned within a first angled slot of the second plurality of angled slots, and wherein at least one of the second plurality of protruding members is positioned within a second angled slot of the second plurality of angled slots. As mentioned elsewhere herein, some embodiments may comprise four shutters, two of which oppose one another in a first direction and two of which oppose one another in a second direction at least substantially perpendicular to the first direction.

The first and second shutters may at least partially define a collimation aperture, and the apparatus may be configured such that rotation of the first rotatable disk results in movement of the first shutter to alter a size of the collimation aperture, and such that rotation of the second rotatable disk results in movement of the second shutter to alter a size of the collimation aperture. The apparatus may be configured to deliver overlapping radiation comprising x-ray electromagnetic radiation from the x-ray generator and visible electromagnetic radiation from the visible light generator. The collimation aperture may be configured to deliver the visible electromagnetic radiation in a visible target shape and to deliver the x-ray electromagnetic radiation in an x-ray target shape, wherein the size of the visible target shape varies according to the size of the collimation aperture, and wherein size of the x-ray target shape also varies according to the size of the collimation aperture. In this manner, a user may be able to visualize and alter, if necessary, the bounds of the x-ray beam being delivered by the apparatus.

In still another example of an embodiment of an x-ray apparatus, the apparatus may comprise an x-ray generator configured to generate x-ray electromagnetic radiation, a visible light generator configured to generate visible electromagnetic radiation, and a projection member comprising a material at least partially transparent to visible light. The projection member may comprise an image positioned within the path of the visible electromagnetic radiation so as to project a secondary image comprising a shadow defined by the image. In some embodiments, the projection member may comprise a reticle.

The apparatus may also comprise a ranging beam configured to deliver a visible light beam at an angle relative to the visible electromagnetic radiation such that the visible light beam intersects at least a portion of the secondary image at a predetermined distance from the ranging beam. In some embodiments, the ranging beam may comprise a LASER configured to deliver a LASER beam at an angle relative to the visible electromagnetic radiation such that the LASER beam intersects at least a portion of the secondary image at a predetermined distance from the LASER.

The x-ray apparatus may comprise a handheld x-ray apparatus. For example, the apparatus may comprise a handle configured to allow a user to hold and operate the x-ray apparatus with one hand. With respect to such embodiments, the ranging beam may be positioned on the handle. The handle may comprise a base configured to allow the x-ray apparatus to be placed upon a flat surface with only the base in contact with the flat surface, and the LASER may be positioned on the base.

In embodiments in which the projection member comprises a reticle, the reticle may comprise a plurality of non-equidistant dash lines. The non-equidistant dash lines may be spaced apart by a greatest amount at a lower portion of the reticle and wherein the spacing between the non-equidistant dash lines grows progressively smaller from the lower portion of the reticle to an upper portion of the reticle. The apparatus may be configured such that at least some of the non-equidistant dash lines represent equidistant distances away from the x-ray generator and/or another fixed portion of the apparatus.

To provide a more specific example, in some embodiments, the reticle may comprise a first dash line, a second dash line positioned adjacent to the first dash line, and a third dash line positioned adjacent to the second dash line. The first dash line may be spaced apart from the second dash line by a first length, the third dash line may be spaced apart from the second dash line by a second length less than the first length. In such embodiments, the apparatus may be configured such that an object intersecting the LASER beam at the first dash line is separated from the x-ray generator or another fixed point on the apparatus by a first distance, an object intersecting the LASER beam at the second dash line is separated from another fixed point on the apparatus by a second distance, and an object intersecting the LASER beam at the third dash line is separated from another fixed point on the apparatus by a third distance. The difference between the first distance and the second distance may be at least substantially identical to the distance between the second distance and the third distance. In some such embodiments, the reticle may therefore be configured such that the spacing with respect to adjacent dash lines is non-equidistant, but the corresponding distances between the locations at which the ranging beam intersects such adjacent dash lines are equidistant.

Some embodiments may further comprise a collimation aperture configured to deliver overlapping radiation comprising x-ray electromagnetic radiation from the x-ray generator and visible electromagnetic radiation from the visible light generator. The size of the secondary image may vary according to the size of the collimation aperture.

In another specific example of an embodiment of an x-ray apparatus, the apparatus may comprise an x-ray generator configured to generate x-ray electromagnetic radiation, a visible light generator configured to generate visible electromagnetic radiation, and a reticle comprising a material at least partially transparent to visible light. The reticle may comprise a plurality of non-equidistant dash lines positioned within the path of the visible electromagnetic radiation so as to project an image comprising a shadow defined by the dash lines. Such a plurality of dash lines may comprise a first dash line, a second dash line positioned adjacent to the first dash line, wherein the first dash line is spaced apart from the second dash line by a first length, and a third dash line positioned adjacent to the second dash line, wherein the third dash line is spaced apart from the second dash line by a second length. The first length may be greater than the second length such that the dash lines are non-equidistant.

The apparatus may further comprise a ranging beam configured to deliver a visible light beam at an angle relative to the visible electromagnetic radiation such that the visible light beam intersects at least a portion of the image at a predetermined distance from the ranging beam. The apparatus may be configured such that an object intersecting the ranging beam at the first dash line is separated from another fixed point on the apparatus by a first distance, such that an object intersecting the ranging beam at the second dash line is separated from another fixed point on the apparatus by a second distance, and such that an object intersecting the ranging beam at the third dash line is separated from another fixed point on the apparatus by a third distance. The difference between the first distance and the second distance may be at least substantially identical to the distance between the second distance and the third distance.

Another embodiment may comprise an x-ray generator configured to generate x-ray electromagnetic radiation, and a visible light generator, such as an LED, that is configured to generate visible electromagnetic radiation. The apparatus may further comprise a projection member comprising a material at least partially transparent to visible light, wherein the projection member comprises an image positioned within the path of the visible electromagnetic radiation so as to project a secondary image comprising a shadow defined by the image. The apparatus may also comprise a ranging beam configured to deliver a visible light beam at an angle relative to the visible electromagnetic radiation such that the visible light beam intersects at least a portion of the image at a predetermined distance from the ranging beam.

Some embodiments may also comprise a collimator. Such a collimator may comprise one or more rotatable disks. The collimator may further comprise a first shutter at least partially defining a collimation aperture, wherein the first shutter is operably coupled with a first rotatable disk such that rotation of the first rotatable disk moves the first shutter to alter a size of the collimation aperture. Similarly, a second shutter at least partially defining the collimation aperture may be operably coupled with a second rotatable disk such that rotation of the second rotatable disk moves the second shutter to alter a size of the collimation aperture. The apparatus may be configured such that the collimation aperture at least partially defines a size of the secondary image and such that the collimation aperture at least partially defines a size of an x-ray target shape delivered by the x-ray generator.

As described earlier, rotation of the first rotatable disk through a first angle may result in movement of the first shutter of a first distance, and rotation of the second rotatable disk through the first angle may result in movement of the second shutter of a second distance, wherein the first distance differs from the second distance. As also described above, the first rotatable disk may comprise a first plurality of angled slots and a second plurality of angled slots. The first shutter may comprise a first plurality of protruding members, wherein at least one of the first plurality of protruding members is positioned within a first angled slot of the first plurality of angled slots. At least one of the first plurality of protruding members may be positioned within a second angled slot of the first plurality of angled slots.

The first angled slot may extend towards a center of the first rotatable disk at a first angle, and the second angled slot may extend towards the center of the first rotatable disk at a second angle, wherein the first angle is greater than the second angle.

Like other embodiments previously described, the first rotatable disk may comprise a plurality of protrusions positioned along at least a portion of a perimeter of the first rotatable disk, and the second rotatable disk may comprise a plurality of protrusions positioned along at least a portion of a perimeter of the second rotatable disk. The first plurality of protrusions may protrude beyond the perimeter adjacent to the protrusions, and may be configured to allow a user to rotate the first rotatable disk in order to alter a size of the collimation aperture. Similarly, the second plurality of protrusions may be configured to allow a user to rotate the second rotatable disk in order to alter a size of the collimation aperture. In some embodiments, the first plurality of protrusions may be configured to have a distinct tactile feel relative to the second plurality of protrusions such that a user can distinguish the first plurality of protrusions from the second plurality of protrusions by way of tactile feel alone.

DETAILED DESCRIPTION

In the following description, numerous specific details are provided for a thorough understanding of the various embodiments disclosed herein. The systems and methods disclosed herein can be practiced without one or more of the specific details, or with other methods, components, materials, etc. In addition, in some cases, well-known structures, materials, or operations may not be shown or described in detail in order to avoid obscuring aspects of the disclosure. Furthermore, the described features, structures, or characteristics may be combined in any suitable manner in one or more alternative embodiments.

The present disclosure describes various examples of apparatus, systems, and methods relating to the delivery of radiation, such as x-ray radiation, for medical diagnosis and/or treatment. Details of certain embodiments will now be described in greater detail with reference to the accompanying drawings. FIG. 1 depicts an x-ray apparatus at 100. As shown in this figure, x-ray apparatus 100 comprises a handle 110, a collimator 120, cage 170, and inclinometer 175. Cage 170 may comprise an at least partially conical shape. In some embodiments, the shape of cage 170 may at least substantially coincide with the shape of the x-ray beam delivered from x-ray apparatus 100.

Knowledge of the angle of inclination of an x-ray apparatus can be extremely important for certain types of x-rays. For example, in podiatry, it is often necessary to take an x-ray with the x-ray source located at a specific, known angle relative to the patient's foot. Additionally, for certain x-rays, it may be desirable for the user of an x-ray apparatus to know the angle at which an x-ray is taken in order that subsequent x-rays of the same patient may be taken at the same angle. Thus, embodiments of x-ray apparatus may comprise an inclinometer 175 to provide a user with information about the angle at which x-ray radiation is being delivered.

Inclinometer 175 may be used to measure such an angle of inclination of x-ray apparatus 100 at the time of exposure with respect to the ground (perpendicular to the direction of the force of gravity). Inclinometer 175 may immediately provide an indication to a user of the angle of inclination for the orientation of the imaged object.

Inclinometer 175 may comprise four angle pointers which pivot on a central axle and may be weighted to maintain its orientation to the natural horizon during movement of the x-ray apparatus 100. In some embodiments, the four angle pointers may allow the angle of inclination to be read from any position, including for example from the top, bottom, or side of the device. This feature may be provided in some embodiments by having one or more of the pointers extend away from the body/frame of x-ray apparatus, and by providing a transparent window that allows for viewing the pointers not only from the face of inclinometer 175 but also from above or below inclinometer 175.

In some embodiments, one or more sensors may be provided adjacent to particular locations on inclinometer 175. Such sensors may sense the location of one or more of the pointers and may transfer this information to a CPU and/or memory of the device. This information may then, in some embodiments, be transferred to one or more displays, such as a digital display, to provide information to the user about the angle of inclination. This data may also be stored by x-ray apparatus 100 and electronically linked with a particular x-ray image so that a physician or other such person may be able to view an inclination angle while viewing a particular x-ray image.

Inclinometer 175 may be permanently affixed to the x-ray apparatus 100 or, alternatively, may comprise a portable, stand-alone device that can be attached to x-ray apparatus 100. X-ray apparatus 100 and/or inclinometer 175 may therefore comprise a clip or other temporary mounting means that allows inclinometer 175 to be removably attached to a particular location on x-ray apparatus 100. Once imaging is completed, or once the angle is noted, inclinometer 175 may be removed from x-ray apparatus 100 and retained by the user for a later use.

As mentioned above, x-ray apparatus 100 may further comprise a memory module which is configured to record and store the angle of inclination at the time of imaging. This module and/or another such module may also be configured to link the angle with the image. X-ray apparatus 100 may also include an output module for passing the angle of inclination to another device to upload the information for later use.

Inclinometer 175 may have one or more angle pointers that pivots on a central axle and are weighted to maintain their respective orientations to the natural horizon. The angle pointers on the depicted embodiment extend from the central axle at 0, 90, 180, and 270 degrees. When x-ray apparatus 100 is tilted or angled, the angle pointers remain at their original orientations with respect to the horizon, but their positions relative to the markers/display on inclinometer 175 change to display the angle at which the x-ray apparatus 100 is located relative to the horizon.

Inclinometer 175 may also comprise a clear cover having one or more angle indicators with degree markings which may be used to accurately read the angle of inclination. The degree markings may surround the outer edge of the cover and be on at least one of the side and face of the cover. The cover may be divided into four equal quadrants. The degree markings may indicate degrees from zero to 45 degrees and then back to zero degrees, such markings may be in five degree increments. The degree markings may be of different lengths to indicate different increments. The user may be able to visually read the angle by looking through the cover and noting which degree marking the angle pointer is closest to.

Since inclinometer 175 has four different quadrants and four pointers the angle can be read from the top, bottom, or either side of the display. This feature may be useful for a handheld x-ray apparatus, such as x-ray apparatus 100. As a user moves the apparatus, the user may use the device to easily note the angle of inclination.

Handle 110 comprises a handle base 112 comprising a battery 114. Handle 110 may be configured to allow the x-ray apparatus 100 to be stably positioned upon a flat surface with only the base 112 (battery 114 and/or the bottom surface of the remaining portion of base 112 in the absence of battery 114) in contact with the flat surface.

A trigger 116 may also be provided. Trigger 116 may be used to initiate generation of x-ray or other radiation from the device. Trigger 116 may also, or alternatively, be used to actuate and/or alter a feature of some other mechanism, such as a ranging beam 113—which is shown positioned on handle base 112 in FIG. 2—and/or a visible light generator 190. In some embodiments, trigger 116 may comprise multiple parts that may be actuated independently. Alternatively, or additionally, trigger 116 or one or more subparts to trigger 116 may be configured such that a first pull or a partial pull results in actuation of a first mechanism and a second pull or a further pull results in actuation of a second mechanism.

Figure 2:
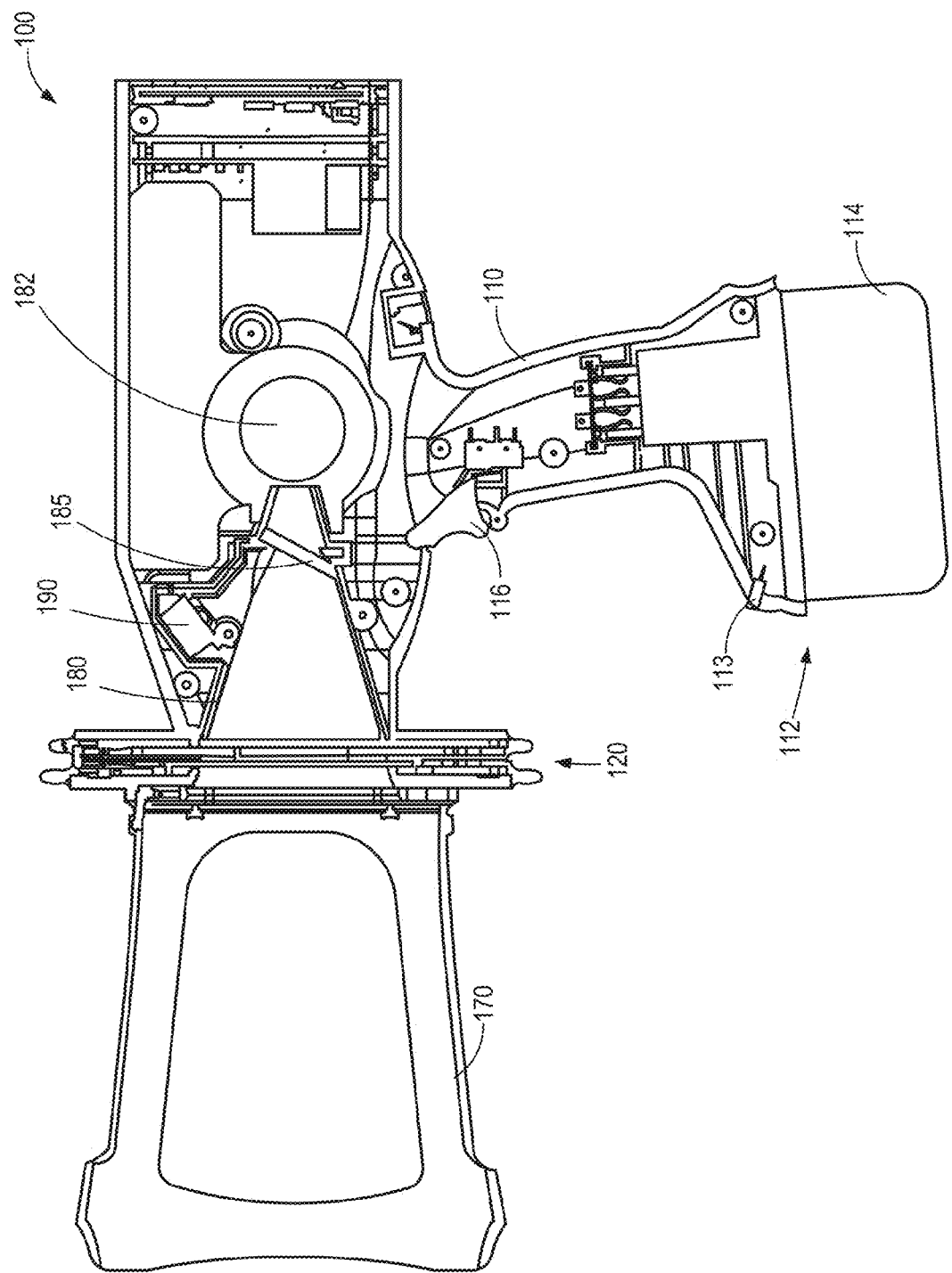
FIG. 2 is a cross-sectional view of the x-ray apparatus depicted in FIG. 1.

FIG. 2 is a cross-sectional view of x-ray apparatus 100. As shown in this figure, x-ray apparatus 100 further comprises an x-ray delivery shield 180 configured to deliver x-ray radiation from an x-ray source 182. As those of ordinary skill in the art will appreciate, x-ray source 182 may comprise an electron-beam vacuum tube that generates x-rays when an electron beam impinges on a metal anode. Other examples of x-ray sources include radioactive isotopes, synchrotrons, or other radiation-generating machines, secondary x-ray sources, such as those generated by x-rays, charged particles, gamma-rays, or other higher-energy radiation impinging on a material that then fluoresces secondary x-rays, and spark-gaps or other electrical discharge sources that generate x-rays.

X-ray apparatus 100 may be configured to deliver x-ray radiation in the form of a cone directed towards an object to be examined or towards an x-ray-sensitive sensor, such as a photographic plate or a digital sensing means, for example. X-ray source 182 may be configured to emit x-ray radiation from one point on x-ray source 182. In order to facilitate delivery of x-ray radiation in the form of a cone, x-ray delivery shield may have an at least substantially conical, or frusto-conical, shape. The radiation cone may generally have crosswise dimensions which are greater than the dimensions of the object to be examined or the sensing means.

A mirror 185 may be positioned within x-ray delivery shield 180. Mirror 185 may be positioned and configured to reflect light from a visible light generator 190. In some embodiments, visible light generator may comprise an LED. Mirror 185 may also be configured so as to be transparent, or at least substantially transparent, to x-ray radiation, such that mirror 185 may be positioned such that x-ray source 182 may deliver x-ray radiation that passes through mirror 185 before being delivered outside of x-ray apparatus 100.

In some embodiments, mirror 185 may also comprise a silver coating, such as a silver oxide coating. In some embodiments, the x-ray source/generator 182 may be positioned away from a center of mirror 185 by a first distance and the visible light generator 190 may be positioned away from the center of the mirror by a second distance that is at least substantially identical to the first distance. In some embodiments, mirror 185 may also be angled and/or otherwise configured such that visible light being delivered from x-ray apparatus 100 is delivered in an at least substantially conical shape that may be at least substantially identical to the shape of the x-ray beam being delivered from x-ray apparatus 100. X-ray delivery shield 180 may also contribute to forming a desirable shape, such as a conical shape, for the visible light being delivered from the device by way of visible light generator 190.

Figure 3:
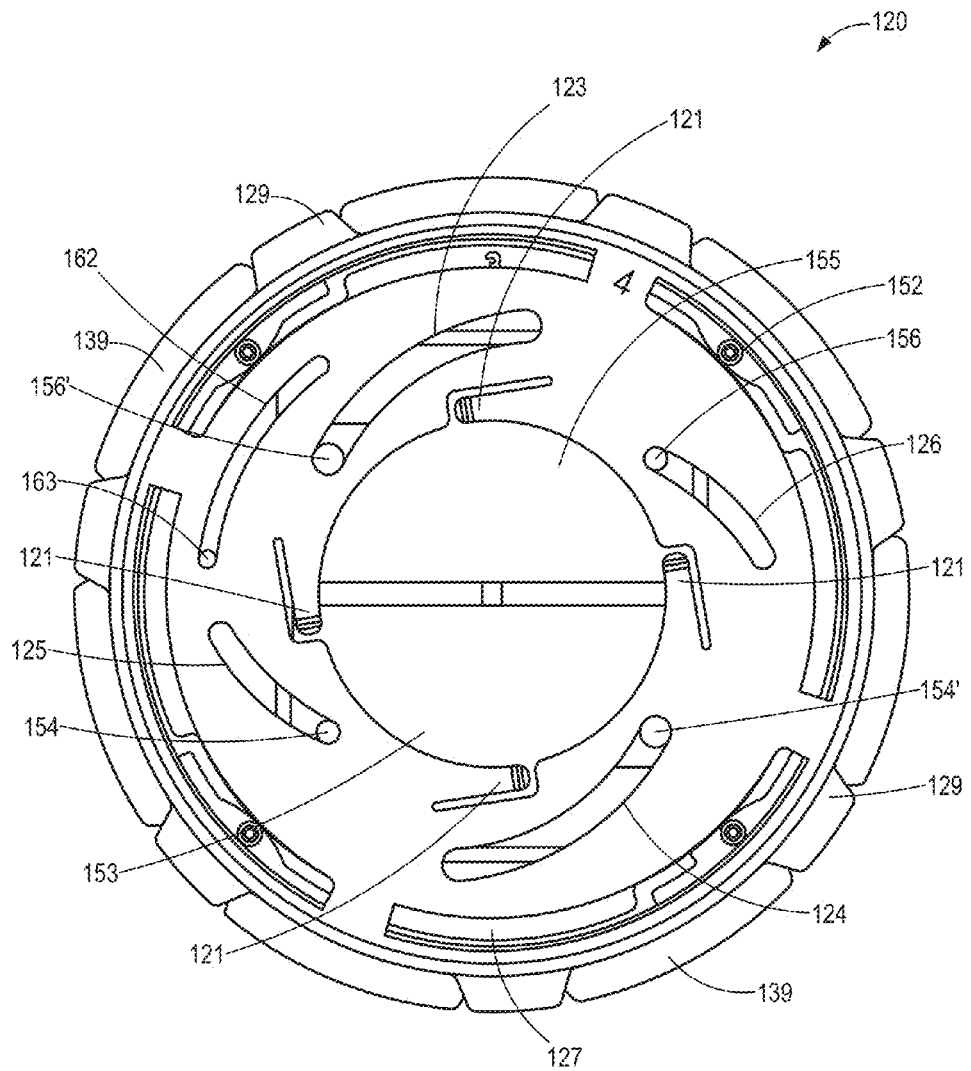
FIG. 3 is a perspective view of one embodiment of a collimator for use in connection with an x-ray apparatus.
Figure 4:
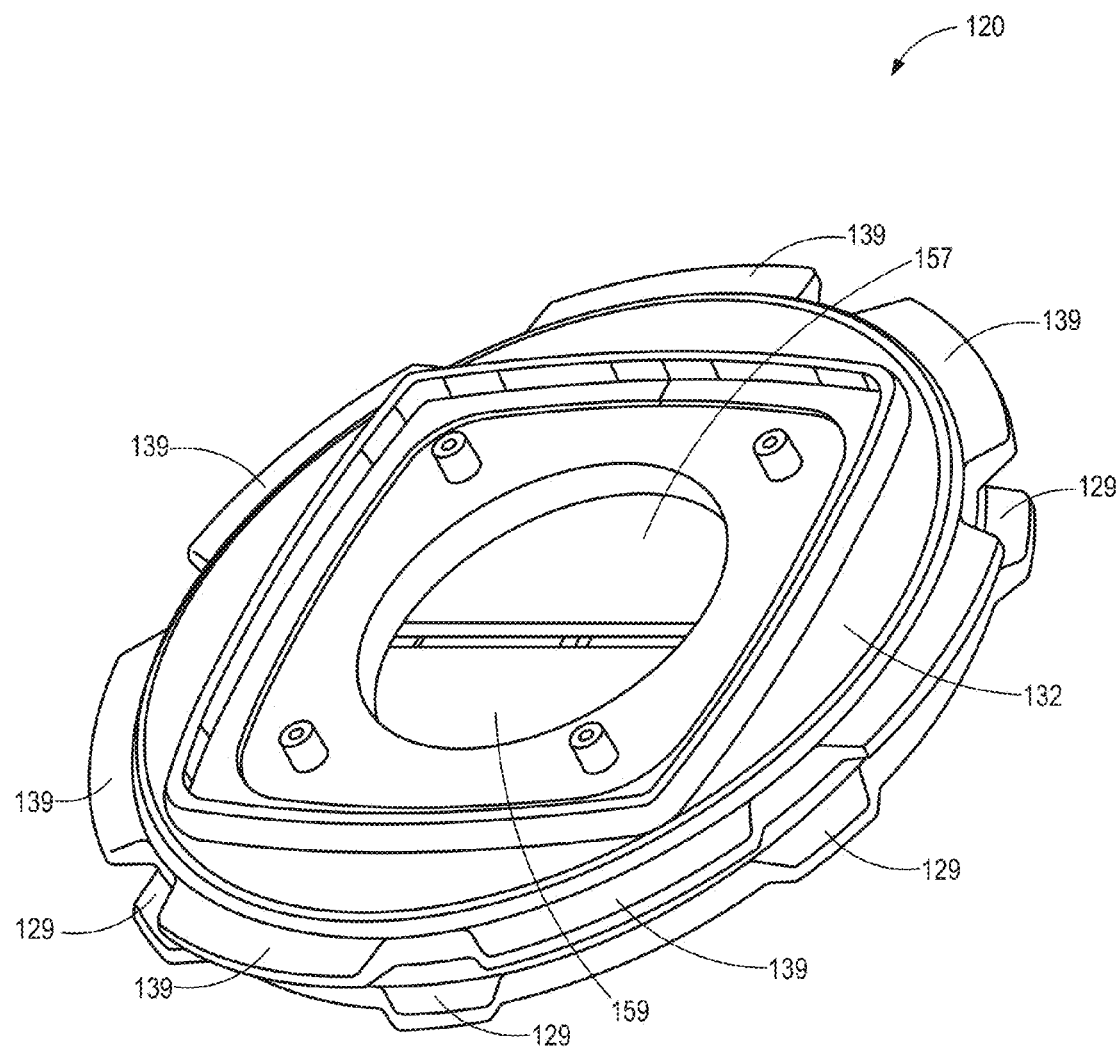
FIG. 4 is another perspective view of the collimator depicted in FIG. 3, shown from the side opposite to the side depicted in FIG. 3.
Figure 5:
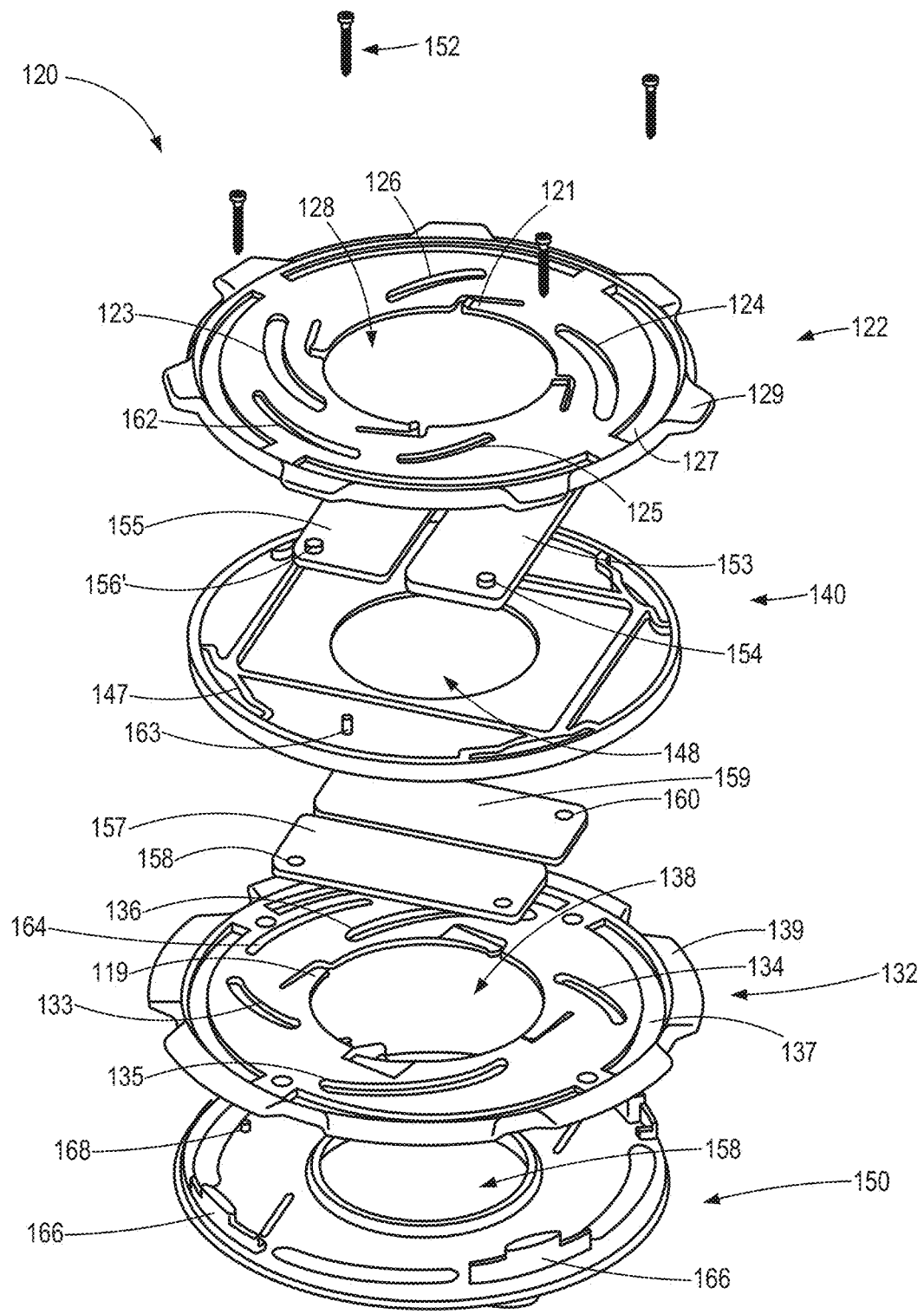
FIG. 5 is an exploded view of the collimator depicted in FIGS. 3 and 4.

FIGS. 3-5 depict an embodiment of a collimator 120. As described in greater detail below, collimator 120 may be positioned between x-ray source 182 and the object to be examined and/or treated with the x-ray radiation. This may allow for a portion of the x-ray beam to be blocked off whereby radiation is only, or at least primarily, applied to the object to be examined inside an examination region or in a region corresponding to a radiation sensor. Collimator 120 may be adjustable to allow for different examinations.

The ideal dimensions of an x-ray signal are often dependent on the particular application involved. For example, in certain types of diagnostic radiology, an x-ray beam having a relatively large pattern may be used to produce images of relatively large portions of a patient's body. At other times, a smaller and more focused x-ray beam may be used to produce detailed images of relatively small portions of a patient's body, such as regions of the head, for instance. The adjustment of collimator 120 may also protect the safety of a patient and/or healthcare provider from unnecessary radiation exposure. It may therefore be desirable for the collimator 120 to be capable of a high degree of positional accuracy to ensure an accurate x-ray dosage to the patient through a well-defined aperture, and to prevent accidental exposure of others.

The rotatable disks may be made of any material that allows the parts to function as described herein, such as polyethylene or another polymer, for example.

It should also be noted that other embodiments are contemplated that are not limited to collimating x-rays. Other embodiments could also be used for collimating other types of radiation.

As described in greater detail below, the shutters used with collimator 120 may be at least substantially planar. In some embodiments, one or more horizontal shutters may be provided and one or more vertical shutters may also be provided. The horizontal shutter(s) may be mounted in a common plane, and the vertical shutter(s) are mounted in a common plane parallel to that of the horizontal shutters, but slightly offset to allow the shutters to open and close without mechanical interference. The shutters can be made of any x-ray opaque material. In some embodiments, the rotatable disks may also be made of and/or coated with an x-ray opaque material, but other embodiments are contemplated in which the rotatable disks are not made up of such a material. This is because the device may be configured with an x-ray delivery shield, as discussed below, that may deliver the x-ray radiation in such a manner that the shutters alone, if made up of an x-ray opaque material, are sufficient to fully or at least sufficiently contain the x-ray beam. This may provide for cost savings and/or weight reduction in such embodiments since x-ray opaque materials tend to be more costly and heavier than x-ray transparent materials.

FIG. 3 is a perspective view of collimator 120. FIG. 4 is another perspective view of the collimator depicted in FIG. 3, shown from the side opposite to the side depicted in FIG. 3. FIG. 5 is an exploded view of the collimator depicted in FIGS. 3 and 4. As shown in these figures, collimator 120 comprises a rear rotatable disk 122, a front rotatable disk 132, a center plate 140, and a front disk cover 150. Each of these components comprises a central opening. Namely, rear rotatable disk 122 comprises central opening 128, front rotatable disk 132 comprises central opening 138, center plate 140 comprises central opening 148, and front disk cover 150 comprises central opening 158.

Openings 128, 138, 148, and 158 allow for the passage of x-rays. Although these openings are shown in the drawings as being circular, other embodiments are contemplated in which one or more such openings are of a different shape, including but not limited to a rectangle, oval, etc. The inner edge of one or more of the rotatable disks (i.e. edge surrounding the central openings) may be coated in or otherwise made of an x-ray opaque material.

Front and front rotatable disks 122 and 132, respectively, are each operatively coupled with two separate shutters that are configured to move when the rotatable disks are rotated. More particularly, rear rotatable disk 122 is operatively coupled with shutters 153 and 155. Similarly, front rotatable disk 132 is operatively coupled with shutters 157 and 159.

When rear rotatable disk 122 is rotated in a first direction, shutters 153 and 155 are approximated. Otherwise stated, when rear rotatable disk 122 is rotated in a first direction, shutters 153 and 155 are approximated so as to move in directions at least substantially opposite from one another such that these two shutters close towards one another. When rear rotatable disk 122 is rotated in a second direction opposite from the first direction, shutters 153 and 155 move in directions at least substantially opposite from one another such that these two shutters open away from one another.

Similarly, when front rotatable disk 132 is rotated in a first direction, the other two shutters, namely, shutters 157 and 159, move in directions at least substantially opposite from one another such that these two shutters close towards one another. In addition, when front rotatable disk 132 is rotated in a second direction opposite from the first direction, shutters 157 and 159 move in directions at least substantially opposite from one another such that these two shutters open away from one another. However, shutters 157 and 159 may be configured to move in directions at least substantially perpendicular to the directions in which shutters 153 and 155 move. In some embodiments, shutters 153 and 155 may therefore be configured to move in at least substantially horizontal directions, and shutters 157 and 159 may be configured to move in at least substantially vertical directions when x-ray apparatus 100 is in an upright position.

Some embodiments may further be configured such that the collimation aperture defined by shutters 153, 155, 157, and 159 cannot be fully closed. For example, one or more of the shutters may be configured such that movement in a direction to decrease the size of the collimation aperture is prevented before the collimation aperture is entirely closed by the shutters. This may be useful for certain embodiments that provide a visual indication of an x-ray target to prevent the visual indication from completely disappearing. In this manner, a user may be provided with a visual indication of the treatment/diagnosis area at all times during operation, or at least during all times in which an x-ray beam is being delivered.

In some embodiments, the x-ray apparatus 100 may be configured such that the rear rotatable disk 122 can be rotated independently of the front rotatable disk 132. In addition, in some embodiments, the x-ray apparatus 100 may be configured such that rotation of the rear rotatable disk 122 through a first angle results in movement of the shutters 153 and/or 155 of a first distance, such that rotation of the front rotatable disk 132 through the first angle results in movement of shutters 157 and/or 159 of a second distance, wherein the first distance differs from the second distance.

This feature may be useful for embodiments having a rectangular, non-square field-of-view, such as embodiments designed to match up with a 10 inch×12 inch detector, for example. With regard to such embodiments, it may be useful to configure x-ray apparatus 100 such that the horizontal shutters (shutters 153 and 155, for example) move farther than the vertical shutters (shutters 157 and 159, for example) for the same amount of rotation of the rotatable disks in order to maintain a constant horizontal to vertical "aspect ratio" throughout at least a portion of the whole range of motion.

Some embodiments, however, may be configured such that the aspect ratio changes slightly throughout the rotation. For example, in some embodiments, the largest size of the collimation aperture may be a rectangle with a given aspect ratio, such as 10×12, and the smallest size of the collimation aperture may a square. Thus, the two rotatable disks may be configured such that equal rotation angles result in different shutter movement speed (due to different slot angling between the front and rear rotatable disks) to allow for constant adjustment of the aspect ratio between the two terminal positions. In other embodiments, the x-ray apparatus 100 may be configured such that the vertical shutters stop moving before the horizontal shutters stop moving so as to allow the aperture to be changed from its smallest possible rectangular, non-squared shape to a corresponding minimally-sized square. In such embodiments, the aspect ratio, and the shutter movement speed per given rotation, may be constant throughout the rotation movement until the movement is stopped on one of the rotatable disks.

FIGS. 3-5 also depict a series of angled slots. More particularly, rear rotatable disk 122 comprises angled slots 123-126 and front rotatable disk 132 comprises angled slots 133-136. Each of the shutters comprises a plurality of protruding members. Namely, shutter 153 comprises two opposing protruding members, identified at 154 and 154' in the drawings and, similarly, shutter 155 comprises two opposing protruding members identified at 156 and 156'. Likewise, shutter 157 comprises two opposing protruding members 158 and shutter 159 comprises two opposing protruding members 160.

In embodiments configured to provide for a constant aspect ratio, the angled slots 123-126 of rear rotatable disk 122 may comprise angles that differ from the angles of angled slots 133-136 of front rotatable disk 132. By providing, for example, for steeper angled slots on a rotatable disk that is operably coupled with vertical shutters, such vertical shutters may be configured to move a greater distance with an equivalent amount of rotation relative to the horizontal shutters in order to provide for a collimation aperture with at least a substantially constant aspect ratio.

Other embodiments may be configured such that the front and front rotatable disks are coupled with one another such that rotation of one disk results in rotation of the other disk. Such embodiments may further be configured, if desired, to maintain a constant aspect ratio. For example, a rotation of a first disk may result in a greater amount of rotation of a second disk. Similarly, a rotation of the second disk may result in a lesser amount of rotation of the first disk in order to maintain a constant aspect ratio.

The term "slot" is intended to be broadly interpreted to include any type of channel, hole, track, or sliding mechanism that allows the protruding members to slide or otherwise move within the slot and to transfer a rotational motion to an appropriate translation or other movement of one or more corresponding shutters. The angled slots may be of an appropriate length to allow the shutters to move from a fully open position to a closed, or a nearly closed position.

The protruding members may, in some embodiments, be made of the same material as the shutters, and may be integrally formed with the shutters in some embodiments. Alternatively, the protruding members may be attached to a shutter, for example, by an adhesive, and be made up of any material which allows them to slide within an angled slot. Although the protruding members in the depicted embodiment are circular, it should be noted that the protruding members could be any shape or size that allows them to slide within an angled slot.

In some embodiments, at least one of a first plurality of protruding members of a single shutter may be positioned within a first angled slot of the first plurality of angled slots, and at least one of the first plurality of protruding members of the same shutter may be positioned within a second angled slot of the first plurality of angled slots. This configuration may provide stability to prevent the shutter from pivoting with respect to a single protruding member and/or to prevent binding of the shutters.

For example, in the depicted embodiment, two separate protruding members 154 and 154' of a single shutter 153 may be positioned within two different angled slots of rear rotatable disk 122, namely, angled slots 124 and 125. Similarly, two separate protruding members 156 and 156' of another single shutter 155 may be positioned within two different angled slots of rear rotatable disk 122, namely, angled slots 123 and 126.

With respect to the shutters operatively coupled with the front rotatable disk 132, the configuration may operate in a similar manner. For example, two separate protruding members 158 of shutter 157 may be positioned within two different angled slots, namely, angled slots 133 and 135. Similarly, two separate protruding members 160 of another shutter 159 may be positioned within two different angled slots, namely, angled slots 134 and 136.

In some embodiments, x-ray apparatus 100 may be configured such that one or more of the angled slots extends towards the center of its respective rotatable disk at a different angle than one or more other such angled slots. For example, in some embodiments, a first angled slot may extend towards a center of the rear rotatable disk 122 at a first angle and a second angled slot may extend towards the center of the rear rotatable disk 122 at a second angle that differs from the first angle. In some such embodiments, the first angled slot may have a first radius of curvature, the second angled slot may have a second radius of curvature, and the first radius of curvature may be greater than the second radius of curvature.

For example, with reference again to the collimator 120 depicted in FIGS. 3-5, opposing slots 125 and 126 of rear rotatable disk 122 extend towards center opening 128 at a steeper angle/rate than opposing slots 123 and 124. Similarly, opposing slots 133 and 134 of front rotatable disk 132 extend towards center opening 138 at a steeper angle/rate than opposing slots 135 and 136. This configuration may be desirable in order to maintain a substantially parallel movement of one or more shutters during rotation of the disk that is operatively coupled therewith.

In some embodiments, one or more of the slots of a particular rotatable disk may also have a different width than one or more of the remaining slots of the rotatable disk. For example, as best seen in FIG. 3, opposing slots 125 and 126 in rear rotatable disk 122 are narrower than opposing slots 123 and 124. Similarly, as best seen in FIG. 5, opposing slots 133 and 134 in front rotatable disk 132 are narrower than opposing slots 135 and 136.

One or more of the protruding members may similarly have a greater width than one or more of the remaining protruding members of a particular shutter and/or those operatively coupled with a particular rotatable disk. For example, with reference again to FIG. 3, one of the two protruding members 154' may be wider than the other protruding member 154 on the same shutter 153. Likewise, one of the two protruding members 156' on shutter 155 may be larger than the other protruding member 156. As such, collimator 120 may be configured such that the larger of the two protruding members on shutter 155 (protruding member 156') will not fit within slot 126 and the larger of the two protruding members on shutter 153 (protruding member 154') will not fit within slot 125. This configuration may be substantially repeated on the front rotatable disk 132. This configuration may be useful in facilitating assembly of collimator 120, including restricting or preventing misassembly of collimator 120.

As further depicted in FIGS. 3-5, front rotatable disk may comprise one or more assembly slots 127 and 162. Assembly slots 127 are positioned around the periphery of rotatable disk 122 and extend in a curved path at least substantially corresponding to the curvature of rotatable disk 122. One or more of the peripheral assembly slots 127 may be configured to have a larger size than the remaining peripheral assembly slots 127. In this manner, proper assembly of collimator 120 may be facilitated and misassembly prevented or at least reduced.

For example, one or more protruding assembly pieces 166 may be positioned to extend from another portion of the device, such as from the front disk cover 150 in the depicted embodiment. Protruding assembly pieces 166 may be configured to extend through one or more other pieces in the assembly making up collimator 120. For example, protruding assembly pieces 166 may extend through peripheral assembly slots 137 in front rotatable disk 132, through peripheral assembly slots 147 in center plate 140, and then through peripheral assembly slots 127 in rear rotatable disk 122. In embodiments in which one or more of the peripheral assembly slots 127 is larger than the remaining slots, a corresponding number of protruding assembly pieces 166 may be larger than the remaining protruding assembly pieces. In this manner, incorrect assembly can be prevented or at least reduced.

To further reduce the possibility of incorrect assembly, another assembly slot 162 may be formed on rear rotatable disk 122. Similarly, another assembly slot 164 may be formed on front rotatable disk 132. Assembly slot 162 may be configured to receive a pin 163, or another equivalent protruding member, formed on center plate 140. A similar pin 168 or equivalent protruding member may be formed on front disk cover 150 and may be configured to be received within a similar assembly slot 164 formed within front rotatable disk 132. By positioning assembly slot 162 at a different location and/or with different dimensions relative to assembly slot 164, misassembly of x-ray apparatus 100 may be prevented or at least inhibited.

One or more fastening members 152 may also be used to secure the various components of collimator 120 together. In addition, one or more spring members 121 may be formed upon one or more of the components making up collimator 120. For example, in the depicted embodiment, rear rotatable disk 122 comprises four spring members 121 that extend towards the exterior of collimator 120. Similarly, front rotatable disk 132 comprises four spring members 119 that extend towards front disk cover 150. Spring members 119 and 121 may help prevent collimator 120 and/or one or more of its internal components from being broken or rattling during use. These components may also allow for gaps in the parts stack to improve tolerance requirements. In addition, spring members 121 may allow for wear over time without allowing various components of the mechanism to become loose or damaged.

In some embodiments, one or more of the rotatable disks may further comprise a plurality of protrusions positioned along at least a portion of a perimeter of the rotatable disk(s). Such protrusions may be configured to protrude beyond the perimeter of the rotatable disk(s) adjacent to the protrusions. These protrusions may be configured to allow a user to rotate the rotatable disk(s) in order to alter a size of the collimation aperture.

For example, in the depicted embodiment, a plurality of protrusions 129 are positioned along the perimeter of rear rotatable disk 122 and a plurality of protrusions 139 and positioned along the perimeter of front rotatable disk 132.

Protrusions 129 and/or 139 may comprise tabs, knobs, handles, or teeth, for example, that extend from an outer edge of a rotatable disk. As shown in the accompanying drawings, the rotatable disks may be shaped like a sprocket and may have many protrusions extending from the outer edge of the disks. The protrusions may allow the disks to be rotated by hand in either a clockwise or counter-clockwise direction. The protrusions may be used to simplify manual adjustment of the circular disk and to provide a visual indicator of the shutter positions. The protrusions and/or another component of the collimator that does not rotate with the protrusions may have markings and/or indentations to indicate the location of the shutters in a particular configuration. In some embodiments, the protrusions may be engaged with a motor or other mechanical actuation means to provide for automated movement of the disks, and therefore shutters.

The protrusions of one rotatable disk may be configured to have at least one of a different shape and a different size relative to the protrusions of another rotatable disk. In this manner, a user may be able to see and/or feel the difference between the two sets of protrusions to provide information about which shutter or shutters will be opened or closed by rotating the disk associated with the protrusions.

For example, in the depicted embodiment, protrusions 129 are smaller than protrusions 139. In addition, the device is configured such that protrusions 129 can be positioned within recesses defined by protrusions 139 in a particular configuration. X-ray apparatus 100 may, in some embodiments, be configured such that each configuration in which protrusions 129 are interleaved between protrusions 139 is a stable configuration. In other words, the device may be configured such that rotation of one of the rotatable disks with respect to the other continues in a smooth manner until protrusions 129 are positioned in between protrusions 139, at which point the two disks have a tendency to stay in such a configuration and additional force is required to continue such a rotation action. In some embodiments, each stable configuration in which protrusions 129 are positioned in between protrusions 139 may correspond with a particular, desired size of the collimation aperture, such as a size corresponding to a common treatment, diagnosis, and/or sensor size at a particular distance. In some embodiments, markings may also be provided on the protrusions and/or on another part of the device that does not rotate with the rotatable disks in order to provide information to a user about the size/status of the collimation aperture.

Figure 6:
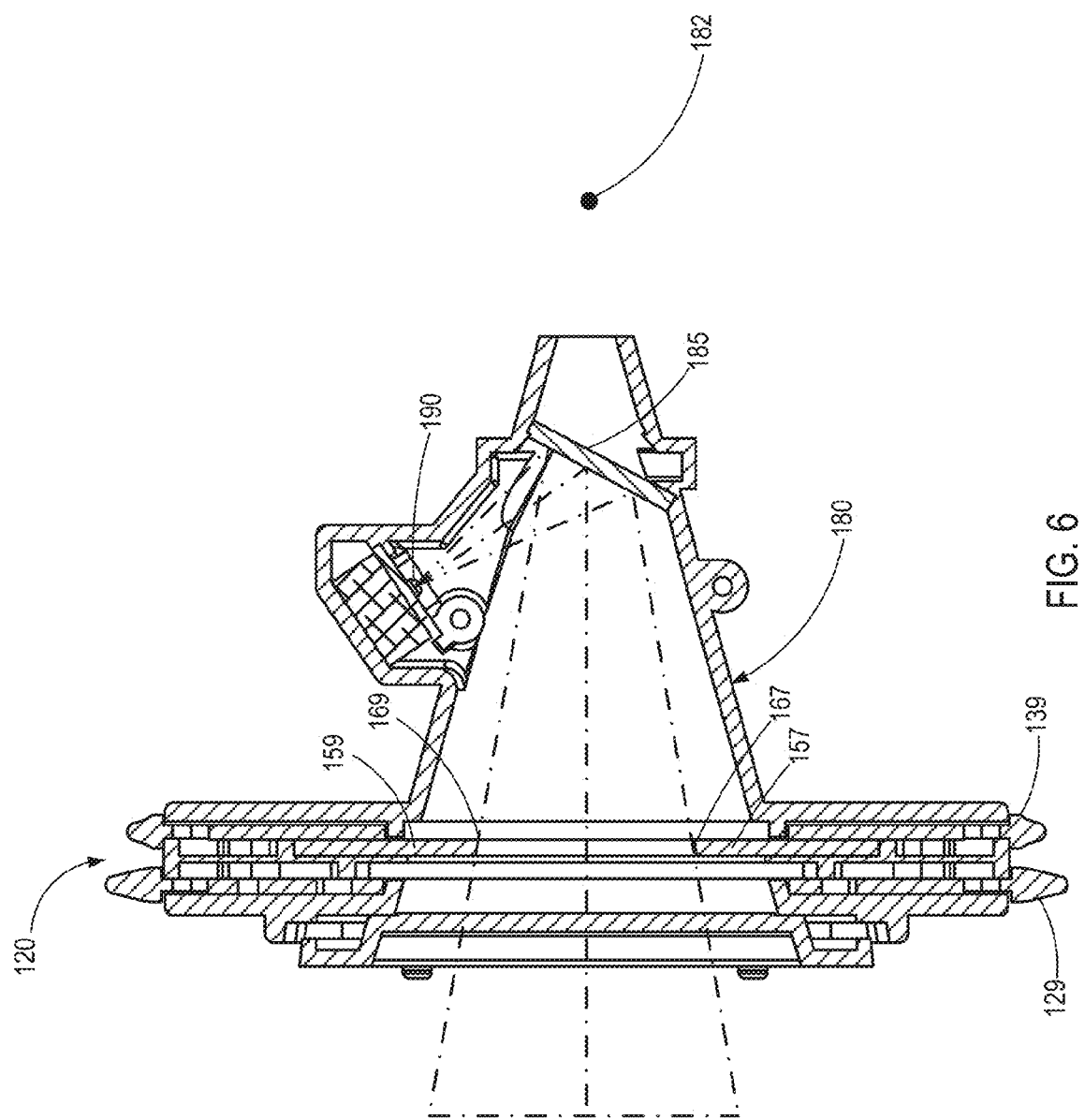
FIG. 6 is a cross-sectional view depicting certain internal components, including an x-ray source and a visible light generator, according to one embodiment of an x-ray apparatus.

FIG. 6 is a cross-sectional view depicting certain internal components of an embodiment of an x-ray apparatus, including x-ray source 182, which is depicted as a point source, mirror 185, visible light generator 190, and x-ray delivery shield 180. FIG. 6 also depicts certain components of collimator 120. As this figure indicates, light from visible light generator 190 is directed towards mirror 185, which is positioned at an appropriate angle to direct such light towards an exit defined at least partially by x-ray delivery shield 180. X-ray radiation from x-ray source 182 is also delivered through x-ray delivery shield 180, and may be delivered through mirror 185, which may be transparent to x-ray radiation.

As further indicated in this figure, one or more of the shutters used with collimator 120 may have angled edges in order to provide more well-defined borders to a visible light target shape delivered by visible light generator 190 through collimator 120, and/or to similarly provide more well-defined borders to an x-ray target shape delivered by x-ray source 182 through collimator 120. For example, as shown in FIG. 6, instead of being at right angles relative to the front and back surfaces of shutters 157 and 159, edge 167 of shutter 157 is angled and edge 169 of shutter 159 is angled to at least substantially match the angle of the conical shape of visible light delivered by visible light generator 190 and/or to at least substantially match the angle of the conical shape of x-ray radiation delivered by x-ray source 182. It should be further understood that, although the edges of shutters 153 and 157 of rear rotatable disk 122 are not visible in FIG. 6, such edges may be similarly angled such that all four sides (four embodiments having a collimation aperture defining a rectangular-shaped target shape) of the target shape have relatively well-defined borders.

Figure 7:
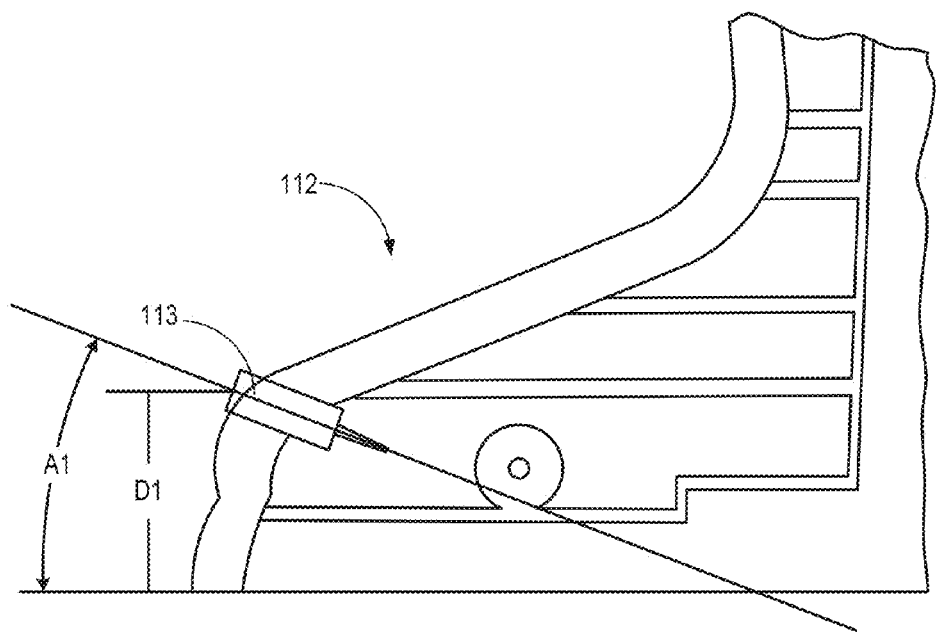
FIG. 7 is a close-up, cross-sectional view of a base including a LASER according to one embodiment of an x-ray apparatus.

FIG. 7 is a close-up, cross-sectional view of a handle base 112 including a ranging beam 113 according to one embodiment of x-ray apparatus 100. Ranging beam 113 may comprise a LASER. As shown in the figure, LASER 113 is positioned at a distance D1 from a bottom surface of handle base 112 and is angled upward from the bottom surface of handle base 112. The angle at which LASER 113 is angled upward is A1. As those of ordinary skill in the art will appreciate, the values of D1 and A1 may be adjusted so as to configure the ranging beam 113 to intersect the projection of reticle or another projection member image at a desired distance.

Ranging beam 113 may be configured to deliver a visible light beam, such as a LASER in certain embodiments, at an angle relative to the visible electromagnetic radiation delivered by visible light generator 190 such that the visible light beam from ranging beam 113 intersects at least a portion of a projected image projected by visible light generator 190 at a predetermined distance from the devices, such as from ranging beam 113, for example. In this manner, a user may be able to visualize one or more distances at which a treatment, diagnosis, or other similar use of the device may be applied.

The ranging beam 113 and related concepts presented herein may be used on an x-ray apparatus, as described in great detail herein, but may also be useful on other devices such as rifles and other firearms, photography, lab equipment, and other applications where it is useful to determine and provide a visualization of a distance from an object.

In addition, although ranging beam 113 is shown as being located near the bottom of handle 110 in the handheld x-ray apparatus 100 depicted in the drawings, in other embodiments the ranging beam 113 may be located elsewhere on the device. For example, in a non-handheld x-ray apparatus, the ranging beam may be located above or below the clear window of the projection member at an appropriate distance to intersect the crosshair reticle or other projected image. The ranging beam may be at a fixed location and angle or, in other embodiments, the location and/or angle of the ranging beam may be adjustable. Further, the apparatus may be configured such that the ranging beam adjustments may be done by hand or the device may include an adjustment module which is configured to adjust the laser to a specific angle automatically after receiving user input for a desired angle and/or distance.

For example, in some embodiments, the x-ray apparatus may comprise a user input that allows a user to input a particular angle and/or focus distance. The ranging beam may then be configured to automatically adjust to the distance and/or angle input in order to place the ranging beam at the center of the reticle or projected image from the projection member at the distance input. Similarly, the x-ray apparatus may be configured such that the ranging beam is manually adjustable and the angle is automatically translated into a distance measurement at which the ranging beam will intersect a particular portion of the projected image, such as at the center of a cross-hair reticle. The distance may then be provided to the user on a display.

Figure 8:
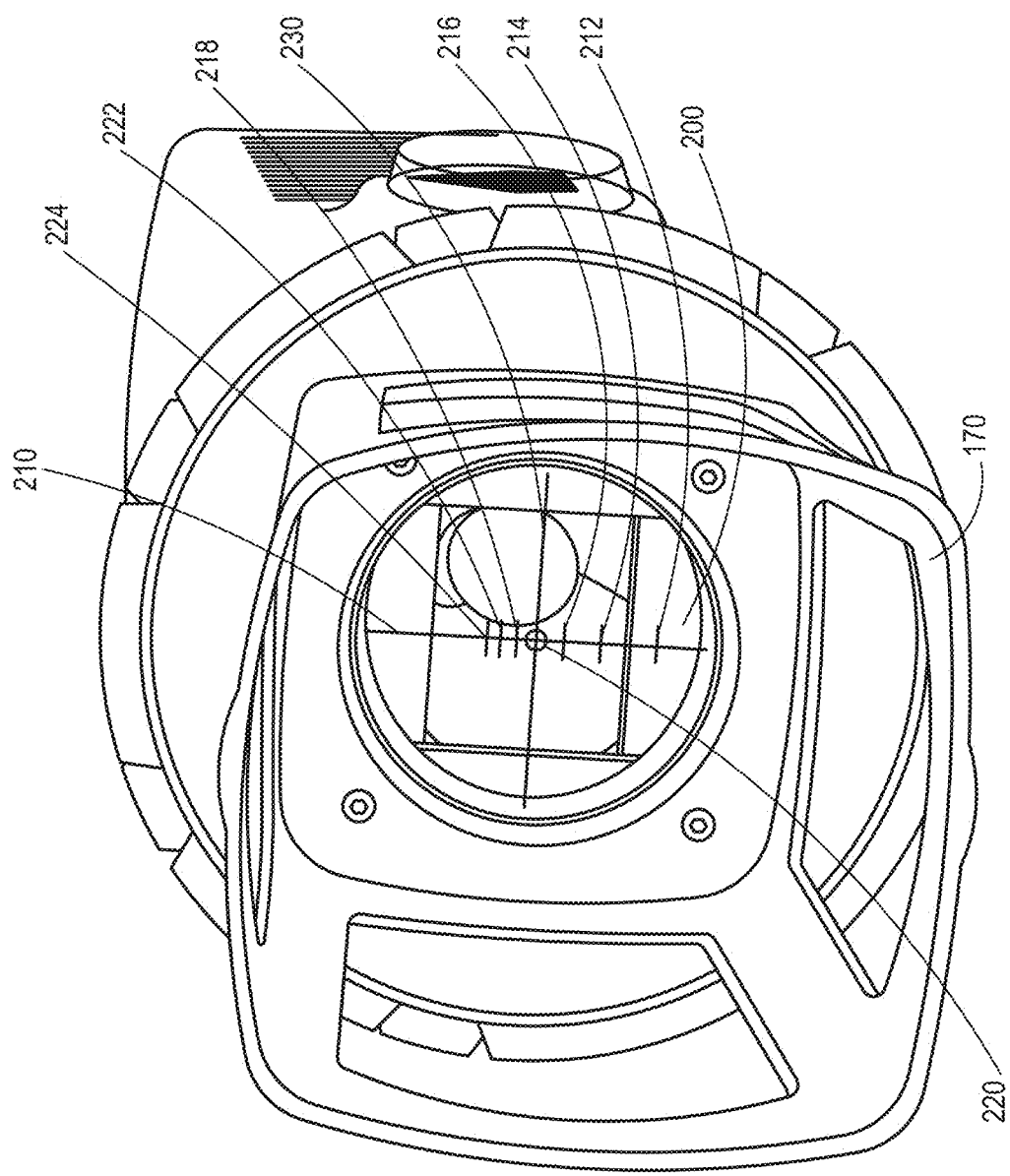
FIG. 8 is a perspective view depicting a reticle of one embodiment of an x-ray apparatus.

X-ray apparatus 100 may also be configured with a projection member that may be configured to work in conjunction with visible light generator 190 in order to project an image that may be used with ranging beam 113 to determine a desired treatment/diagnosis distance. For example, FIG. 8 is a perspective view depicting one embodiment of a projection member 200. Projection member 200 comprises a reticle. However, it should be understood that a wide variety of alternative projection members may be used, as will be apparent to one of ordinary skill in the art after having received the benefit of this disclosure.

A light field may be transmitted through reticle 200, which may comprise a clear window, to thereby project an image of the reticle on a wall or object. As described elsewhere herein, a LASER or another ranging beam may be placed outside of the light field and directed at an angle towards the light field. The ranging beam may be positioned and angled to intersect a specific location along the projected reticle. The angle of the ranging beam can be adjusted to insure that the intersection of the projected reticle and laser is at the specific distance.

The clear window may be made of any material that is transparent to both visual light and x-rays, such as glass or polycarbonate for example, to allow the light field and x-ray field to travel through without being distorted. The clear window may have a reticle, such as a cross-hair reticle, or another projection member printed, etched, or otherwise disposed on the clear window. The cross-hair reticle may be any desirable pattern or grid.

The intersection of two primary cross-hairs may delineate the center of the clear window, and may also delineate the center of the x-ray field when the x-ray apparatus is in use.

Projection member 200 may comprise a material at least partially transparent to visible light. The projection member 200 may also comprise an image positioned within the path of visible electromagnetic radiation, such as light from visible light generator 190 so as to project an image comprising a shadow defined by the image. For example, in embodiments in which projection member 200 comprises a reticle, such as the embodiment depicted in FIG. 8, the image may comprise a plurality of dash lines that may be projected in an image with the dash lines defining shadows from light generated from visible light generator 190.

The ranging beam and the projected cross-hair reticle or other projected image from a projection member may create a parallax effect. This parallax effect can be used to define a specific distance from the x-ray device where the ranging beam and the projected cross-hair reticle intersect. The target intersection of the ranging beam and projected cross-hair reticle may therefore be configured to take place at a specific desired distance. The location and/or angle of the ranging beam can be adjusted so the intersection occurs at the center of the cross-hair reticle, or at a different marking on the projected cross-hair reticle.

Once the target intersection is known and the device is in use, the intersection of the ranging beam and cross-hair reticle can be adjusted by moving the x-ray device closer or further away from the starting location. For example, in some embodiments, a LASER may be positioned at a specific angle to intersect the cross-hair reticle at 28 inches from the x-ray source. The distance of 28 inches may be chosen for certain applications because this may be the distance necessary to produce a 10 inch by 12 inch x-ray size, a common size used in the detector industry. In this embodiment, the specific angle of the LASER may be about 19.5 degrees from the natural horizon. The center of the cross-hair reticle may be projected 28 inches in front of the x-ray radiation source.

In some embodiments, the cross-hair reticle and laser may be fixed in location such that the angle and location can only be adjusted before the device is in use. A user can move the x-ray device closer or further away from the starting location until the LASER intersects the projected cross-hair reticle at the center marking, thereby ensuring that the x-ray radiation source is 28 inches from the intersection.

In embodiments in which the projection member comprises a reticle, the reticle may comprise a plurality of non-equidistant dash lines. For example, with reference again to the embodiment depicted in FIG. 8, reticle 200 comprises a plurality of non-equidistant dash lines positioned along a vertical cross bar 210. Vertical cross bar 210, along with a corresponding horizontal cross bar 230, may together define cross hairs defining a target. The target area defined by vertical cross bar 210 and horizontal cross bar 230 may be further delineated by a target marker 220. In the depicted embodiment, target marker 220 comprises a circle. By providing a target marker 220, a user may be able to position x-ray apparatus 100 such that a LASER or another light projected from ranging beam 113 hits a particular location on a patient's body or on a sensor with the LASER positioned within the bounds of target marker 220 in order to precisely determine a desired treatment/diagnosis area.

The non-equidistant dash lines may be spaced apart by a greatest amount at a lower portion of the reticle 200. The spacing between the non-equidistant dash lines may also grow progressively smaller from the lower portion of the reticle 200 to an upper portion of the reticle 200. For example, in the embodiment depicted in FIG. 8, dash line 212, which is the lower-most dash line in reticle 200, is positioned adjacent to dash line 214 by a first distance. Dash line 216 is positioned adjacent to dash line 214 by a second distance less than the first distance. Dash line 216 is positioned adjacent to horizontal cross marker 230 (which may, in some embodiments, also serve functionally as a dash line) by a third distance less than the second distance. Similarly, dash line 218, which is above horizontal cross bar 230, is positioned adjacent to horizontal cross bar 230 by a fourth distance less than the third distance. Dash line 222 is positioned adjacent to dash line 218 by a fifth distance less than the fourth distance. And, finally, dash line 224 is positioned adjacent to dash line 222 by a sixth distance less than the fifth distance.

In some embodiments, the positioning of the non-equidistant dash lines may be specifically configured such that at least some of the non-equidistant dash lines represent equidistant distances away from the x-ray generator and/or another fixed point on the apparatus. In other words, the placement of the non-equidistant dash lines may be precisely determined to allow a user to precisely determine various distances away from the apparatus.

Figure 9:
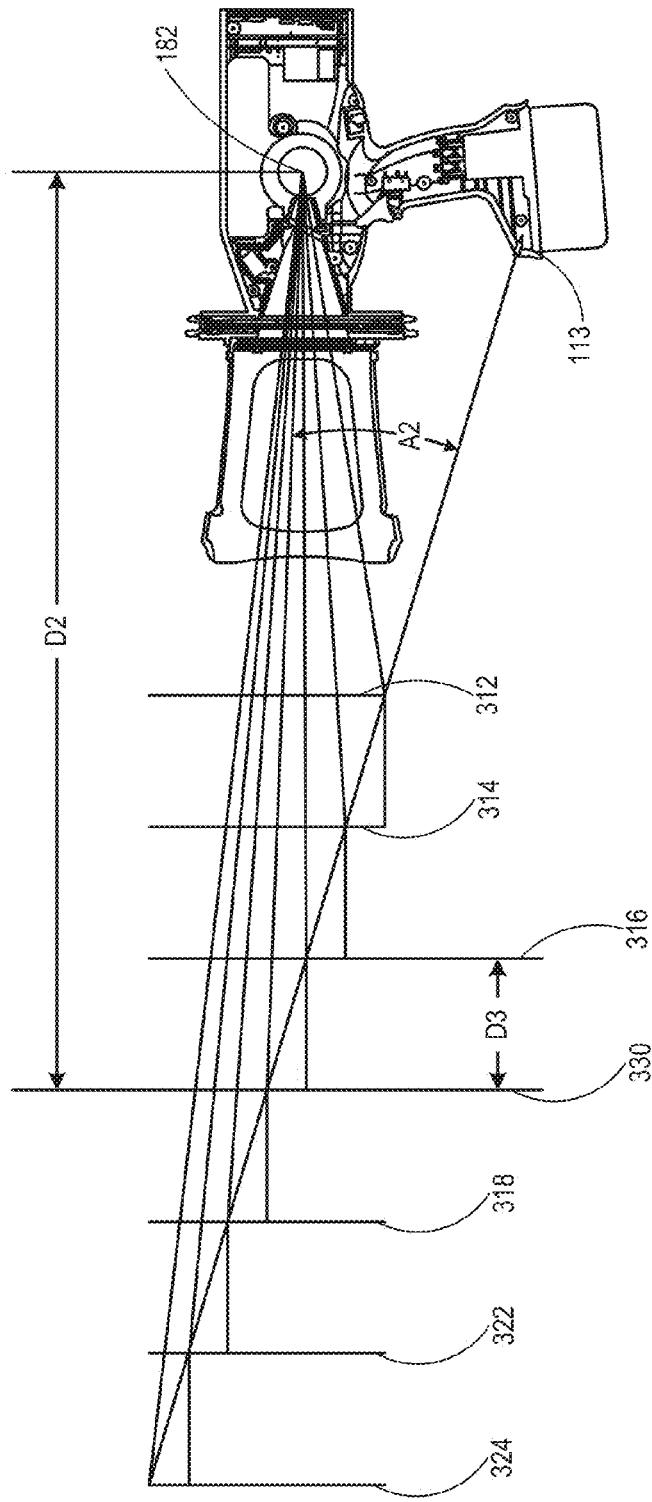
FIG. 9 depicts certain distance characteristics relating to one embodiment of an x-ray apparatus comprising a reticle having non-equidistant dash lines.

A more specific example is shown in FIG. 9, which may be referenced in conjunction with FIG. 8 in order to obtain a full understanding of the operation of one embodiment. As shown in FIG. 9, a series of equidistant distance markers are depicted that correspond with the non-equidistant dash lines of reticle 200, as depicted in FIG. 8. More particularly, distance marker 330 corresponds with horizontal cross bar 230. Thus, at distance D2, light from ranging beam 113 intersects the projection of the image on reticle 200 at cross bar 230. Similarly, distance marker 312 from FIG. 9 corresponds with dash line 212 from FIG. 8, distance marker 314 corresponds with dash line 214, distance marker 316 corresponds with dash line 216, distance marker 318 corresponds with dash line 218, distance marker 322 corresponds with dash line 222, and distance marker 324 corresponds with dash line 224.

Each of the adjacent distance markers depicted in FIG. 9 therefore corresponds with adjacent dash lines from reticle 200. Each of these distance markers is separated from an adjacent distance marker by the same distance, namely, D3. In this manner, a user can not only confirm one distance that may correspond with the center of the projected image from the reticle, but can confirm a series of distances and can move a target patient, sensor, or another target item closer to, or away from, the device by precise multiples of a particular distance. When used in combination with certain embodiments of the collimator discussed above, a user can both determine a precise desired location from the device and visualize the full extend to the area that is to receive x-ray radiation for diagnosis, treatment, or other such uses.

FIG. 9 also depicts an angle A2 between a beam perpendicular to collimator 120 (delivered from x-ray source 182 and/or visible light generator 190) and an angled beam delivered from ranging beam 113. As mentioned above, this angle may be adjusted as desired for a particular application.

The foregoing specification has been described with reference to various embodiments. However, one of ordinary skill in the art will appreciate that various modifications and changes can be made without departing from the scope of the present disclosure. For example, although the embodiment depicted in the accompanying drawings comprises dash lines along a vertical cross bar, other embodiments may additionally, or alternatively, comprise dash lines along the horizontal cross bar. In addition, various operational steps, as well as components for carrying out operational steps, may be implemented in alternate ways depending upon the particular application or in consideration of any number of cost functions associated with the operation of the system. Accordingly, any one or more of the steps may be deleted, modified, or combined with other steps. Further, this disclosure is to be regarded in an illustrative rather than a restrictive sense, and all such modifications are intended to be included within the scope thereof. Likewise, benefits, other advantages, and solutions to problems have been described above with regard to various embodiments. However, benefits, advantages, solutions to problems, and any element(s) that may cause any benefit, advantage, or solution to occur or become more pronounced, are not to be construed as a critical, a required, or an essential feature or element.

It will also be readily understood that the order of the steps or actions of the methods described in connection with the embodiments disclosed may be changed, as would be apparent to those skilled in the art. Thus, any order in the drawings or Detailed Description is for illustrative purposes only and is not meant to imply a required order, unless specified to require such an order.

Those having skill in the art will appreciate that many changes may be made to the details of the above-described embodiments without departing from the underlying principles of the invention. The scope of the present invention should, therefore, be determined only by the following claims.

The invention claimed is:

1. An x-ray apparatus, comprising:
   an x-ray generator configured to generate x-ray electromagnetic radiation;
   a visible light generator configured to generate visible electromagnetic radiation;
   a projection member comprising a material at least partially transparent to visible light, wherein the projection member comprises an image positioned within the path of the visible electromagnetic radiation so as to project a secondary image comprising a shadow defined by the image; and a LASER configured to deliver a LASER beam at an angle relative to the visible electromagnetic radiation such that the LASER beam intersects at least a portion of the secondary image at a predetermined distance from the LASER.

2. The x-ray apparatus of claim 1, wherein the x-ray apparatus comprises a handheld x-ray apparatus.

3. The x-ray apparatus of claim 2, further comprising a handle configured to allow a user to hold and operate the x-ray apparatus with one hand.

4. The x-ray apparatus of claim 3, wherein the LASER is positioned on the handle.

5. The x-ray apparatus of claim 4, wherein the handle comprises a base configured to allow the x-ray apparatus to be placed upon a flat surface with only the base in contact with the flat surface, and wherein the LASER is positioned on the base.

6. The x-ray apparatus of claim 1, wherein the projection member comprises a reticle.

7. The x-ray apparatus of claim 6, wherein the reticle comprises a plurality of non-equidistant dash lines.

8. The x-ray apparatus of claim 7, wherein the non-equidistant dash lines are spaced apart by a greatest amount at a lower portion of the reticle and wherein the spacing between the non-equidistant dash lines grows progressively smaller from the lower portion of the reticle to an upper portion of the reticle.

9. The x-ray apparatus of claim 7, wherein the apparatus is configured such that at least some of the non-equidistant dash lines represent equidistant distances away from the reticle.

10. The x-ray apparatus of claim 9, wherein the reticle comprises:
a first dash line;
a second dash line positioned adjacent to the first dash line, wherein the first dash line is spaced apart from the second dash line by a first length; and
a third dash line positioned adjacent to the second dash line, wherein the third dash line is spaced apart from the second dash line by a second length, and wherein the first length is greater than the second length,
wherein the apparatus is configured such that an object intersecting the LASER beam at the first dash line is separated from the reticle by a first distance, wherein the apparatus is configured such that an object intersecting the LASER beam at the second dash line is separated from the reticle by a second distance, wherein the apparatus is configured such that an object intersecting the LASER beam at the third dash line is separated from the reticle by a third distance, and wherein the difference between the first distance and the second distance is at least substantially identical to the distance between the second distance and the third distance.

11. The x-ray apparatus of claim 1, further comprising a collimation aperture configured to deliver overlapping radiation comprising x-ray electromagnetic radiation from the x-ray generator and visible electromagnetic radiation from the visible light generator, and wherein the size of the secondary image varies according to the size of the collimation aperture.

12. An x-ray apparatus, comprising:
an x-ray generator configured to generate x-ray electromagnetic radiation;
a visible light generator configured to generate visible electromagnetic radiation;
a reticle comprising a material at least partially transparent to visible light, wherein the reticle comprises a plurality of non-equidistant dash lines positioned within the path of the visible electromagnetic radiation so as to project an image comprising a shadow defined by the dash lines, wherein the plurality of non-equidistant dash lines comprises:
a first dash line;
a second dash line positioned adjacent to the first dash line, wherein the first dash line is spaced apart from the second dash line by a first length; and
a third dash line positioned adjacent to the second dash line, wherein the third dash line is spaced apart from the second dash line by a second length, and wherein the first length is greater than the second length; and
a ranging beam configured to deliver a visible light beam at an angle relative to the visible electromagnetic radiation such that the visible light beam intersects at least a portion of the image at a predetermined distance from the ranging beam,
wherein the apparatus is configured such that an object intersecting the ranging beam at the first dash line is separated from the reticle by a first distance, wherein the apparatus is configured such that an object intersecting the ranging beam at the second dash line is separated from the reticle by a second distance, wherein the apparatus is configured such that an object intersecting the ranging beam at the third dash line is separated from the reticle by a third distance, and wherein the difference between the first distance and the second distance is at least substantially identical to the distance between the second distance and the third distance.

13. The x-ray apparatus of claim 12, wherein the ranging beam comprises a LASER.

14. The x-ray apparatus of claim 12, wherein the visible light generator comprises a light-emitting diode.

15. An x-ray apparatus, comprising:
an x-ray generator configured to generate x-ray electromagnetic radiation;
a visible light generator configured to generate visible electromagnetic radiation;
a projection member comprising a material at least partially transparent to visible light, wherein the projection member comprises an image positioned within the path of the visible electromagnetic radiation so as to project a secondary image comprising a shadow defined by the image;
a ranging beam configured to deliver a visible light beam at an angle relative to the visible electromagnetic radiation such that the visible light beam intersects at least a portion of the image at a predetermined distance from the ranging beam;
a first rotatable disk;
a first shutter at least partially defining a collimation aperture, wherein the first shutter is operably coupled with the first rotatable disk such that rotation of the first rotatable disk moves the first shutter to alter a size of the collimation aperture;
a second rotatable disk; and
a second shutter at least partially defining the collimation aperture, wherein the second shutter is operably coupled with the second rotatable disk such that rotation of the second rotatable disk moves the second shutter to alter a size of the collimation aperture, wherein the apparatus is configured such that the collimation aperture at least partially defines a size of the secondary image, and wherein the apparatus is configured such that the collimation aperture at least partially defines a size of an x-ray target shape delivered by the x-ray generator.

16. The x-ray apparatus of claim 15, wherein the apparatus is configured such that the first rotatable disk can be rotated independently of the second rotatable disk.

17. The x-ray apparatus of claim 15, wherein the apparatus is configured such that rotation of the first rotatable disk through a first angle results in movement of the first shutter of a first distance, wherein rotation of the second rotatable disk through the first angle results in movement of the second shutter of a second distance, and wherein the first distance differs from the second distance.

18. The x-ray apparatus of claim 15, wherein the first rotatable disk comprises a first plurality of angled slots, wherein the first shutter comprises a first plurality of protruding members, wherein at least one of the first plurality of protruding members is positioned within a first angled slot of the first plurality of angled slots, and wherein at least one of the first plurality of protruding members is positioned within a second angled slot of the first plurality of angled slots.

19. The x-ray apparatus of claim 18, wherein the first angled slot extends towards a center of the first rotatable disk at a first angle, wherein the second angled slot extends towards the center of the first rotatable disk at a second angle, and wherein the first angle is greater than the second angle.

20. The x-ray apparatus of claim 19, further comprising:
a plurality of protrusions positioned along at least a portion of a perimeter of the first rotatable disk, wherein the first plurality of protrusions protrude beyond the perimeter adjacent to the protrusions, and wherein the first plurality of protrusions are configured to allow a user to rotate the first rotatable disk in order to alter a size of the collimation aperture; and
a second plurality of protrusions positioned along at least a portion of a perimeter of the second rotatable disk, wherein the second plurality of protrusions protrude beyond the perimeter adjacent to the protrusions, wherein the second plurality of protrusions are configured to allow a user to rotate the second rotatable disk in order to alter a size of the collimation aperture, and wherein the first plurality of protrusions are configured to have a distinct tactile feel relative to the second plurality of protrusions such that a user can distinguish the first plurality of protrusions from the second plurality of protrusions by way of tactile feel alone.

* * * * *